United States Patent [19]

Doorakian et al.

[11] 4,130,543
[45] Dec. 19, 1978

[54] AR-CYCLIC SULFONIUM ARENETHIOL SALTS AND THEIR ZWITTERIONS

[75] Inventors: George A. Doorakian, Bedford; Lawrence G. Duquette, Maynard, both of Mass.

[73] Assignee: The Dow Chemical Company, Midland, Mich.

[21] Appl. No.: 673,579

[22] Filed: Apr. 5, 1976

[51] Int. Cl.² ............................................. C08G 65/44
[52] U.S. Cl. ................................... 528/125; 528/171; 528/174; 528/218; 528/220; 528/374; 528/377; 528/380; 32/15; 204/159.11; 260/327 TH; 260/327 M; 260/327 P; 260/327 S; 260/327 B; 260/327 C; 260/329 S; 260/329 HS; 260/330.5; 260/332.3 R
[58] Field of Search ...... 260/329 S, 327 TH, 332.3 R, 260/47 R, 49, 519, 329 HS, 330.5, 327 M, 327 S, 327 B, 327 C; 204/159.11; 428/457

[56] References Cited

U.S. PATENT DOCUMENTS

| | | | |
|---|---|---|---|
| 3,660,431 | 5/1972 | Hatch et al. | 260/332.3 R |
| 3,767,622 | 10/1973 | Hatch et al. | 260/47 R |
| 3,915,991 | 10/1975 | Schmidt et al. | 260/329 S |

Primary Examiner—Lester L. Lee

[57] ABSTRACT

Ar-cyclic sulfonium arenethiol salts exemplified by the formula:

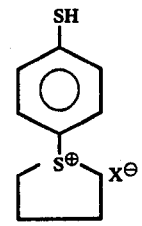

may be converted to their corresponding zwitterion, exemplified by the formula:

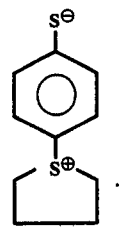

The latter polymerize very readily upon exposure to mild conditions of heat or radiative energy. The resultant polymers are water-insoluble resins useful as adhesives, coatings, films and the like. The zwitterions containing more than one arenesulfide and cyclic sulfonium group per molecule, crosslink upon exposure to heat to form thermoset resins.

14 Claims, No Drawings

AR-CYCLIC SULFONIUM ARENETHIOL SALTS AND THEIR ZWITTERIONS

BACKGROUND OF THE INVENTION

This invention relates to ar-cyclic sulfonium arenethiol salts, their zwitterions and polymers thereof.

The propensity of many sulfonium salts to polymerize upon exposure to heat to yield a polyester and a by-product sulfide has been recognized by Hatch in Canadian Pat. No. 708,230, Lloyd in U.S. Pat. No. 3,409,660 and Kangas in U.S. Pat. No. 3,322,737. More recently in U.S. Pat. Nos. 3,636,052, 3,660,431, 3,723,386 and 3,749,737, it has been recognized that various hydroxyphenyl cyclic sulfonium salts may be converted to phenoxide cyclic sulfonium zwitterions that polymerize upon exposure to heat without yielding sulfide by-products.

Heretofore, the preparation and polymerization of thiophenoxide cyclic sulfonium zwitterions has not been disclosed.

SUMMARY OF THE INVENTION

The present invention, in one aspect, resides in a novel group of ar-cyclic sulfonium mercaptoarene salts characterized by the fact that the aromatic rings thereof bear mercapto and cyclic sulfonium substituents. Specifically, the members of this novel group of cyclic sulfonium salts are generally represented by the structural formula:

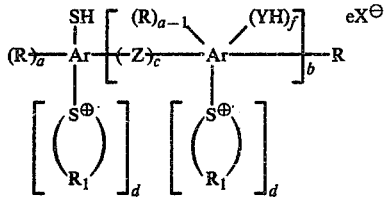

wherein Ar is cyclic aromatic polyyl, each Y is independently sulfur or oxygen, each R is independently a suitably inert monovalent radical capable of existing as a ring substituent on Ar, each $R_1$ is independently a suitably inert divalent organic radical capable of forming a heterocyclic ring containing sulfur, each Z is independently a suitably inert divalent radical bridging the substituted Ar groups, X is a neutralizing anion, each a is independently a positive number corresponding to the number of remaining available ring positions on Ar, b is 0 or a positive number, c is 0 or 1, each d is independently 1 or 2, e is a number such that the salt molecule is electrically neutral, and each f is independently 0 or 1.

For the purposes of this invention, the term "aromatic polyyl" means a polyvalent (more than one) aromatic radical having at least one aromatic carbocyclic ring. For example, benzene as a polyyl has a maximum valence of six, the maximum valence of naphthalene polyyl is eight and the maximum valence of the anthracene polyyl is ten. By a "suitably inert radical" is meant a radical that (1) is inert to the cyclic sulfonium moiety and the mercapto or arene sulfide moiety and (2) does not prevent polymerization of the zwitterion of the aforementioned salt through the cyclic sulfonium moiety.

The foregoing sulfonium salts are readily converted by conventional means to an ar-cyclic sulfonium arylsulfide zwitterion which constitutes a second aspect of this invention. These zwitterions are generally represented by the structural formula:

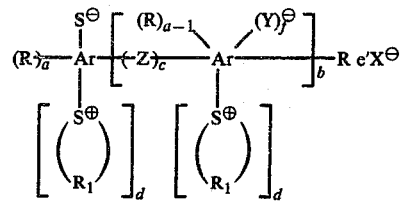

wherein Ar, R, $R_1$, Z, Y, X, a, b, c, d, and f are as defined hereinbefore and e' is a number such that the molecule is electrical neutral.

Surprisingly, the zwitterions of this invention, which are characterized by the presence of the aromatic ring structure bearing an anionic sulfide and a cationic sulfonium group, polymerize upon exposure to thermal or radiation energy which is much less than that required to polymerize zwitterions bearing an anionic oxide instead of the anionic sulfide. If the zwitterion contains an average of two or more anionic groups (sulfide or oxide) and two or more cyclic sulfonium groups per molecule, i.e., b = 1 or more and f = 1, the zwitterion, when heated, crosslinks through these additional groups to form a thermoset resin.

A third aspect of this invention resides in the polymers formed by polymerization of the aforementioned zwitterions. Such polymers are characteristically formed by a ring-opening reaction between the anionic group (sulfide or oxide) and the cyclic sulfonium group to form thioorgano linkages represented by the formula: —SR$_1$Y—.

Solid polymer films and hard surface, adherent coatings exhibiting good impact resistance and resistance to water and various alcohols are obtained by applying the crosslinkable zwitterions to surfaces of a substrate, i.e., metal and thereafter subjecting it to conditions conducive to polymerization. In addition, the aforementioned zwitterions may be combined with conventional cyclic sulfonium zwitterions, e.g., those disclosed in U.S. Pat. Nos. 3,636,052 and 3,660,431 and those derived from the salts of British Pat. No. 1,235,815, and then copolymerized using a conventional polymerization means. Surprisingly, even when relatively small proportions of the zwitterions of the present invention are employed in combination with conventional zwitterions, polymerization is effected at considerably faster rates and at lower temperatures. The zwitterions of the present invention are also useful in the applications described in U.S. Pat. Nos. 3,901,816, 3,900,619, 3,836,385 and 3,804,797.

DETAILED DESCRIPTION OF PARTICULAR EMBODIMENTS

In the ar-cyclic sulfonium arylthiol salts and zwitterions of particular interest, Ar, as depicted in the aforementioned formula, is an aromatic polyyl containing at least one aromatic carbocyclic ring and includes mononuclear aromatic carbocyclic polyyls, polynuclear aromatic carbocyclic or carbocyclic/(N, O or S) heterocyclic polyyl including fused and nonfused polynuclear aromatic polyyls. A carbocyclic/(N, O or S) heterocyclic polyyl is one having at least one carbocyclic ring fused with or bonded to one or more five or six membered aromatic heterocyclic rings, each heterocyclic ring containing only one of N, S or O, provided that the heterocyclic ring containing —N— is a six membered ring similar to pyridine. Examples of suitable carbocyclic/heterocyclic polyyls include polyyls of quinoline, isoquinoline, acridine, benzoquinoline, 1-azophenanthrene, benzofuran, benzothiophene and the like. Preferably Ar is an arene polyyl, e.g., polyyls of benzene, naphthalene, anthracene, biphenyl, and 1,2-diphenylethene. Especially preferred are polyyls of benzene.

R is a suitably inert monovalent radical which is capable of existing as a substituent on Ar. Examples include H, X' wherein X' is haolgen such as Cl or Br, OH, R', —OR', —SR',

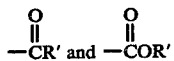

wherein R' is hydrocarbyl or substituted hydrocarbyl. Hydrocarbyl is a monovalent hydrocarbon radical having 1 to 20 carbons, preferably alkyl, cycloalkyl, alkenyl, aryl, alkylaryl, aralkyl and similar hydrocarbon radicals having 1 to 8 carbons. Exemplary substituents of substituted hydrocarbyl are X', OH, —OR', —SR' and the like Preferably X' and R' are as defined hereinbefore. Preferablly R is H, OH, $C_1$-$C_8$ alkyl, $C_1$-$C_8$ alkoxy, Cl, and Br, with H and $C_1$-$C_4$ alkyl being especially preferred. It is understood that the use of R groups other than hydrogen, particularly very bulky groups such as groups larger than $C_4$ hydrocarbyls and ring deactivating groups such as halogen will be limited as necessary to insure formation of a stable ar-cyclic sulfonium arenethiol salt as well as the corresponding zwitterion. While R groups may be in any available ring position on Ar, the R groups other than hydrogen, particularly those R groups more bulky than methyl, are most often in positions that are ortho to the mercapto or anionic sulfide when Ar is benzene polyyl and that are most often in the 3-, 6- or 7-positions when Ar is naphthalene polyyl with positions identified as follows:

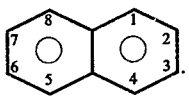

In the salts and zwitterions of this invention, the cyclic sulfonium moiety,

is advantageously a 5- or 6-membered heterocyclic ring that is most often substituted in a ring position that is ortha or para, preferably para, to the mercapto or anionic sulfide moiety (-SH or -S$^\ominus$) or the hydroxyl or anionic oxide moiety when Y is oxygen. Preferably, the cyclic sulfonium moiety is a 5-membered ring.

$R_1$ is any suitably inert divalent organic radical that can exist in a heterocyclic ring containing sulfur. Of course, $R_1$ should not contain bulky and/or reactive groups that would (1) prevent the formation of the stable cyclic sulfonium moiety on Ar or (2) deleteriously affect the ability of the zwitterion to polymerize. Accordingly, $R_1$ is most advantageously hydrocarbylene or substituted hydrocarbylene wherein hydrocarbylene is a divalent hydrocarbon radical. Alternatively, $R_1$ is suitably heterohydrocarbylene or substituted heterohydrocarbylene wherein the chain of the hydrocarbon is interrupted by a hetero atom, e.g., oxygen or sulfur. Hydrocarbylene and heterocarbylene are of sufficient length to provide a 5- or 6-membered ring including

In all suitable $R_1$, the two carbons of $R_1$ bonded to

are methylene. Thus, steric problems which might hinder formation of the zwitterion or polymerization thereof are reduced. Exemplary suitable hydrocarbylenes and heterohydrocarbylenes include alkylene, cycloalkylene, alkenylene, alkylenearylenealkylene, alkenyleneoxyalkylene, and alkylenethioalkylene. When $R_1$ is substituted hydrocarbylene or substituted heterohydrocarbylene, suitable substituents include monovalent radicals given in the definition of R such as OH, —R', —OR', and —SR' wherein R' is hydrocarbyl. Preferably, $R_1$ is a hydrocarbylene such as —(CH$_2$)$_4$—; —(CH$_2$)—$_5$;

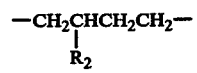

wherein $R_2$ is $C_1$-$C_4$ alkyl such as methyl, ethyl, propyl, or butyl, aryl such as phenyl or chlorophenyl, or alkaryl such as tolyl;

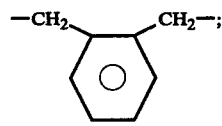

or heterohydrocarbylene such as —(CH$_2$)$_2$—O—(CH$_2$)$_2$—. Of the foregoing radicals, —(CH$_2$)$_4$— and

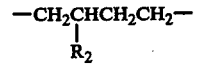

are especially preferred.

Z is a suitably inert divalent radical capable of bridging aromatic rings each bearing a ring substituted sulfide or oxide anion and a cyclic sulfonium cation. Suitable examples of Z include —O—, —S—,

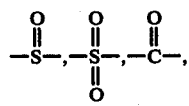

—R$_3$—, —OR$_3$O—, —SR$_3$S—, —R$_3$O—, —R$_3$S—,

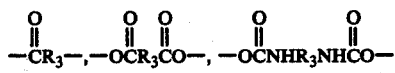

and the like wherein $R_3$ is hydrocarbylene or substituted hydrocarbylene with substituents as defined for R. Advantageously, $R_3$ is hydrocarbylene having 1–8, especially 2–4 carbons. Preferably, Z is —S—, —O—, alkylene, arylene, or oxyalkyleneoxy, with —CH$_2$—, —O(C$_m$H$_{2m}$)O— or

wherein m = 1–8, particularly 2–4, and R″ = C$_1$–C$_4$ alkyl being especially preferred.

X is a neutralizing anion, preferably an inorganic anion such as halide, sulfate, bisulfate, carbonate, bicarbonate, hydroxide and the like.

Some of the most preferred salts and zwitterions are represented by the following generic formulas:

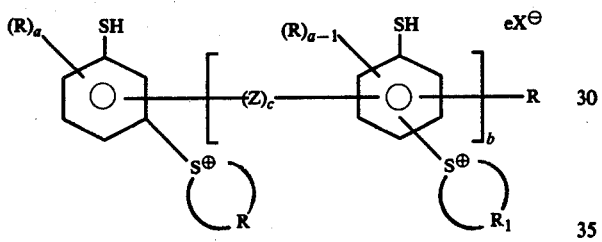

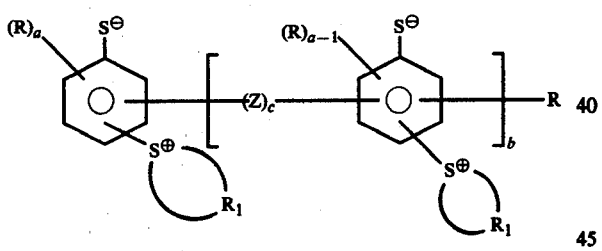

wherein each R, $R_1$, Z, and X are independently as defined hereinbefore.

In the foregoing most preferred zwitterions, a is 3 or 4; c is 0 or 1, preferably. Advantageously, b is zero or a positive number from one up to the highest number of ar-mercaptobenzenes that can be linked together in a linear fashion by direct linkage of benzene groups, i.e., when c=o, or through Z linkages. Depending on the particular Z linkage, b may be as high as 20, but is rarely greater than 5 and most often no more than 1. For example, when Z is —O(C$_m$H$_{2m}$)O— or

as defined hereinbefore, b is preferably 1. When Z is —CH$_2$—, b is 1–20, preferably 1–5. Preferably, each R is independently H, OH, alkoxy, or alkyl. However, it is desirable that no more than one R group per

is OH or alkoxy.

Examples of the most preferred zwitterions are represented by the formulas:

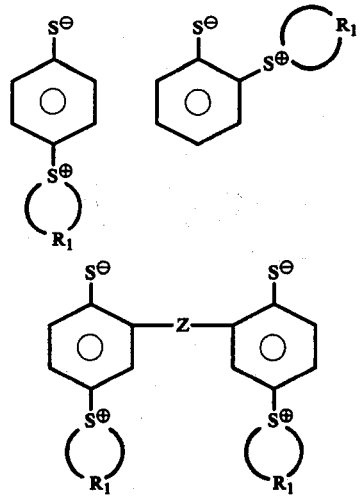

wherein each $R_1$ is independently —(CH$_2$)$_4$—, —(CH$_2$)$_5$—,

—CH$_2$CHCH$_2$CH$_2$—
    |
    $R_2$ wherein $R_2$ is C$_1$–C$_8$ alkyl, aryl such as phenyl or alkaryl such as tolyl;

or —(CH$_2$)$_2$—O—(CH$_2$)$_2$—; and Z is —O(C$_m$H$_{2m}$)O— wherein m = 1–6,

R″
|
—C—
|
R″ wherein R″ is C$_1$–C$_4$ alkyl, or —CH$_2$—. Most preferably, in the aforementioned formulas, each R is independently H or C$_1$–C$_4$ alkyl, especially H; each $R_1$ is independently —(CH$_2$)$_4$— or

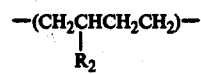

wherein $R_2$ is C$_1$–C$_4$ alkyl; and Z is —O(C$_m$H$_{2m}$)O— wherein m = 2–4,

wherein R" is methyl, or —CH₂—.

Examples of other suitable zwitterions include those represented by the formulas:

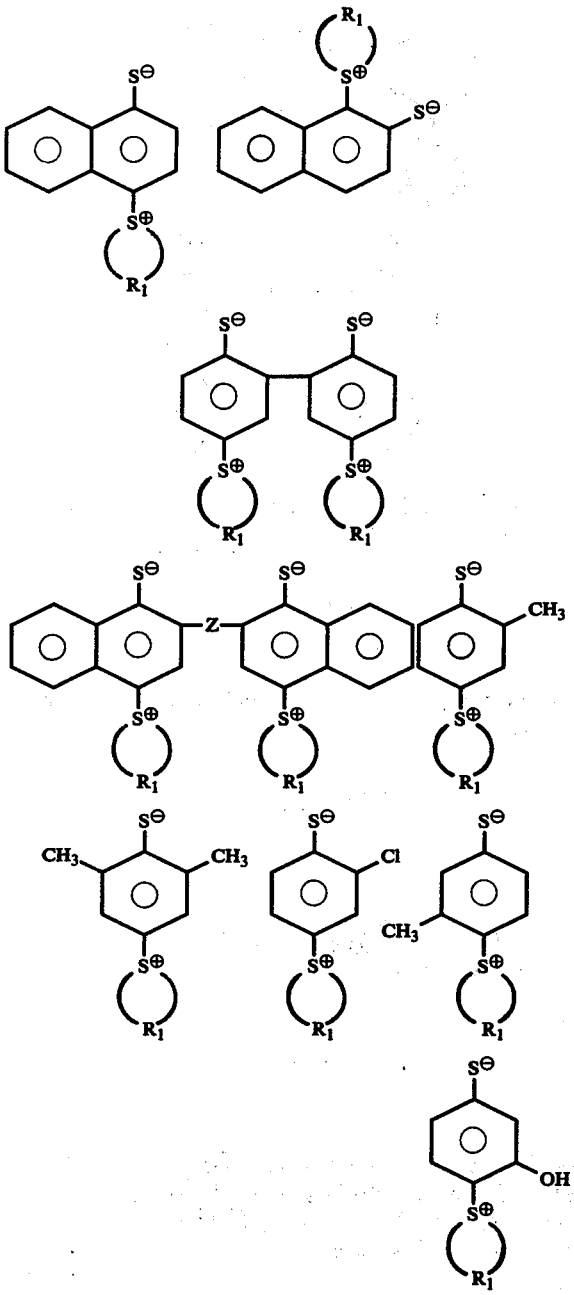

wherein $R_1$ and Z are as defined hereinbefore.

As a general rule, the aforementioned ar-cyclic sulfonium arylthiol salts are most advantageously prepared by the following process:

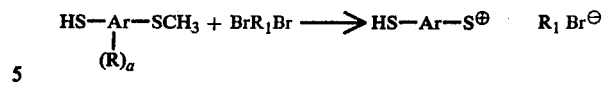

wherein Ar, R, $R_1$ and a are as defined hereinbefore. These processes require that HS—Ar—$(R)_a$ have at least one active ring hydrogen per intended cyclic sulfonium group. To prepare the sulfonium salts having more than one sulfonium group per molecule, it is desirable to substitute a polymercaptoaryl having the formula:

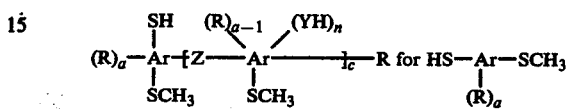

in the aforementioned process.

In the aforementioned process involving the reaction of the alkyl thiomercaptoaryl and the thermally substituted organodihalides such as 1,4-dichlorobutane or 1,5-dibromopentane at an elevated temperature, normally about 100°–200° C, is applicable with many substituted mercaptoaryls in a variety of dihalides. Normally excess dihalide is used as the diluent and recovered along with the byproduct alkylhalide.

Alternatively, when one or more R groups are SH or OH, the additional mercapto or hydroxyl group(s) provide one or more sites for linking molecules of the ar-cyclic sulfonium arylthiol salt as follows:

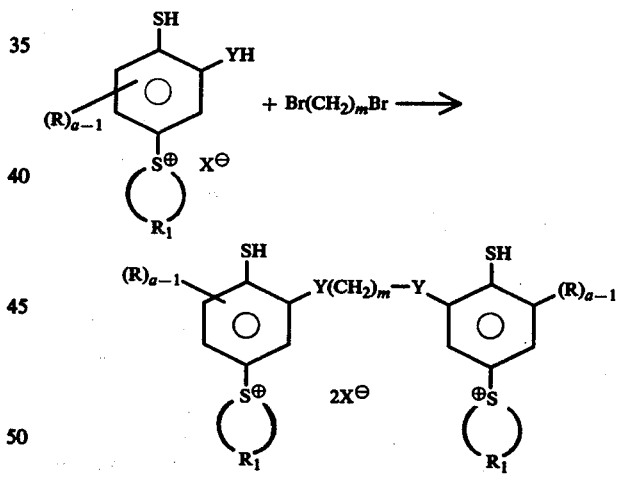

wherein R, $R_1$, Y, X and a are as indicated hereinbefore, m is 1–8, preferably 2–4. Also the additional YH group provides a ready means for placing an alkoxy or alkylthio group on the ring.

In addition to the foregoing methods, the desired zwitterions may be prepared by reacting a protected mercaptoarene with a cyclic sulfide such as tetrahydrothiophene under the conditions similar to those described in U.S. Pat. No. 3,636,052. Subsequently, the protecting group is removed and the resulting sulfonium salt is converted to the zwitterion by contacting it with base. Any group commonly employed to protect mercapto groups is suitable provided that it does not hinder aromatic substitution by the cyclic sulfide.

The aforementioned cyclic sulfonium salts having a nonbasic inorganic anion such as chloride, bromide, perchlorate or bisulfate are generally stable, crystalline salts at room temperature. They are soluble in polar hydroxylic solvents such as water, methanol and isopropyl. Stable mono- or dihydrates have been isolated of some of the chlorides.

Purification of these salts can be achieved by crystallization from a mixed solvent such as methylene chloride/methanol, by conversion into an insoluble salt, e.g., sulfate or perchlorate, or by precipitation from aqueous solution with the precipitate diluent such as dioxane, tetrahydrofuran or higher alcohol.

Conversion of the aforementioned sulfonium salt into the desired reactive zwitterion is achieved by known methods. Ion exchange with an anion exchange resin in hydroxide form is particularly suitable. For some salts direct treatment with a strong inorganic base in a solvent such as anhydrous alcohol, in which the byproduct inorganic solvent has limited solubility, is preferred.

Polymerization of the foregoing zwitterion is readily achieved by the thermal condition employed in the polymerization of the phenoxide cyclic sulfonium zwitterions of U.S. Pat. No. 3,723,386. In addition, the zwitterions of this invention are also readily polymerized by subjecting the zwitterions to radiative energy characteristic of ultraviolet light.

The resulting polymers are generally characterized as containing a plurality of —SR$_1$S— linkages. Most polymers of such zwitterions exhibit physical characteristics similar to those described in U.S. Pat. No. 3,660,431. Copolymers can be made from mixtures of two or more sulfonium zwitterions either blended as finely ground solids or in solution. In general the copolymer properties are immediate between those of the corresponding homopolymers.

Polymers having higher molecular weights are normally obtained by carrying out the polymerization in the absence of oxygen. In some instances, addition of a nucleophilic amine initiator will also increase the molecular weight of the polymer.

Once polymerized, products can be fabricated from the polymer in conventional ways. Alternatively, the zwitterion can be placed in a mold and polymerized in situ. Films can be cast from solutions of the cyclic sulfonium zwitterion in water or some other polar solvents such as methanol, methanol/acetone mixtures, dimethylsulfoxide, etc.

The following examples are given to illustrate the invention and should not be construed as limiting its scope. Unless otherwise indicated, all parts and percentages are by weight.

EXAMPLE 1

A. Preparation of Cyclic Sulfonium Salt

Into a solution of 14 grams (0.1 mole) of 4-methylthiophenol in 75 ml. of dimethylformamide is slowly added 2.8 g. (0.116 mole) of sodium hydride. After hydrogen evolution has ceased, the reaction solution is slowly cooled to 10° C and 12.6 g. (0.1 mole) of dimethylthiocarbamoyl chloride is added. The reaction mixture is then heated at 80° C for 1 hour, and, after cooling, the mixture is poured into 250 ml of 1% KOH. The resulting solution is extracted twice with 100 milliliters of a benzene (4 part)/petroleum ether (1 part), dried over sodium sulfate, and evaporated in vacuum to yield, after washing with petroleum ether, 18.98 g (83.45% yield) of crystalline products having a melting point of 88°–90° C. Spectral and analytical data indicate the crystalline solid to be 4-methylthiophenyl-N,N-dimethylthiooxacarbamate having the structural formula:

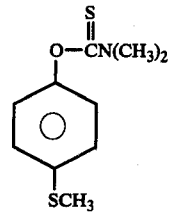

A 14-g portion (0.062 mole) of the aforementioned carbamate is placed in an ampoule, evacuated, sealed and heated at 275° C for 1 hour. Upon cooling the ampoule, there is formed a crystalline product which is then washed with petroleum ether to give a theoretical yield of an off-white crystalline solid having a melting point of 104°–107° C. Spectral and analytical data indicate a crystalline solid to be 4-methylthiophenyl-N,N-dimethylthiocarbamate represented by the structural formula:

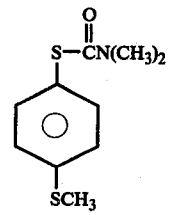

A 14-g portion (0.062 mole) of the aforementioned thiocarbamate is dissolved in 300 ml of methanol containing 56 g of NaOH and is refluxed at 65° C overnight under a dry nitrogen atmosphere. The reaction mixture is filtered, and methanol is evaporated from the resulting filtrate. To the residual oil is added 150 ml of water and then 12 ml of 6 N H$_2$SO$_4$. The resulting mixture is extracted with methylene chloride, washed with water and dried over sodium sulfate. The residue is evaporated in vacuo to yield 8.74 g (92% yield) of a yellow liquid product. Spectral and analytical data indicate the yellow liquid product to be 4-methylthiophenylmercaptan, represented by the structural formula:

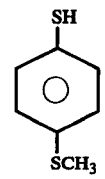

A solution of 0.87 g (0.005 mole) of the aforementioned mercaptan in 8.64 g (0.04 mole) of 1,4-dibromobutane is heated for 6 hours at 120° C resulting in the evolution of methylbromide. The resulting reaction mixture is evaporated to remove excess 1,4-dibromobutane to yield a white residue which is washed thoroughly with methanol. The methanol washings are evaporated to yield an oil which is dissolved in acetone. The acetone solution is cooled to 0° C to yield a white crystalline solid. The crystalline solid is examined by spectral analysis. The 60 mHz proton NMR spectrum (p.p.m. shielding relative to internal TMS in CF$_3$COOD); for H absorption (—CH$_2$—CH$_2$—) at 2.25;

4H absorption (S—CH$_2$—) at 3.50; 4H absorption (aromatic) at 7.20. On the basis of this data the crystalline solid is believed to be (4-mercaptophenyl)tetrahydrothiophenium bromide having the following structure:

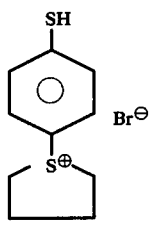

B. Conversion of the Sulfonium Salt to Zwitterion

About 10 ml of a wet, strong base anion-exchange resin in hydroxide form (Dowex ® 1 × 8 resin) is dewatered with methanol and slurried with a methanolic solution of 5 g (0.018 mole) of the aforementioned cyclic sulfonium salt [4-mercaptophenyltetramethylenesulfonium bromide] until a steady pH of 9.2 is attained. The solution is then filtered and concentrated to 3% solids by evaporation under reduced pressure at room temperature. Spectral analysis of the solution indicates conversion of the salts to its zwitterion having the following structural formula:

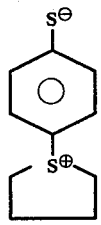

4-(tetrahydrothiophenium)phenylsulfide

C. Polymerization of the Zwitterion

A portion of the 3% methanol solution of the aforementioned zwitterion is applied as a ~.0.5 mil coating onto polystyrene and stainless steel sheets using a #12 Meyer rod. The coated sheets are heated at 40° C for 2 minutes thereby forming a soft, opaque hydrophobic film on the coated substrates.

To a second portion of the 3% methanol solution of the zwitterion is added one part of colloidal silica per part of the zwitterion thereby catalyzing the polymerization of the zwitterion in the methanolic solution at room temperature. Chemical analysis of the resulting homopolymer indicates as follows: calculated: C,61.20; H,6.17; S,32.60. Found: C,61.07; H,6.11; S,32.62.

To 10 parts of a 3% methanolic solution of the aforementioned zwitterion is added one part of a 30% methanolic solution of a bridged resorcinol bifunctional sulfonium-phenoxide monomer represented by the following chemical structure:

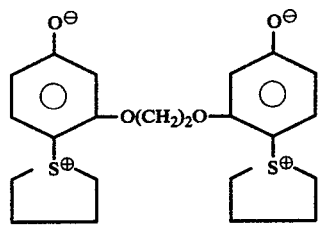

The resultant methanolic solution of the zwitterions is mixed, and a ~0.5 mil coating is applied to a plastic substrate and allowed to dry at 40° C for 5 minutes. The resultant film is hydrophobic, smooth, relatively hard, clear and colorless. Film prepared in a similar manner shows good solvent resistance and good adhesion to metals and plastics.

For purposes of comparison the bridged resorcinol bifunctional sulfonium-phenoxide monomer is homopolymerized and copolymerized with a 4-(tetrahydrothiophenium)phenoxide represented by the following chemical structure:

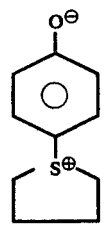

In both instances, polymerization conditions are employed according to the preceding procedure. However, it is noted that in neither case does polymerization occur until the temperature of the film is increased to about 80° C.

As evidenced by the foregoing results, the ar-cyclic sulfonium arylsulfide zwitterions of the present invention polymerize and copolymerize at temperatures significantly below the temperatures required to polymerize the ar-cyclic sulfonium phenoxide zwitterions.

The zwitterions of the present invention are readily applied from aqueous solution and cured within a short time at normal body temperatures. When polymerized, they adhere well to metals, plastics and the like. Accordingly, such zwitterions are very useful as protective coatings for teeth as well as binders in non-mercury containing dental fillings.

What is claimed is:

1. An ar-cyclic sulfonium mercaptoarene salt represented by the formula:

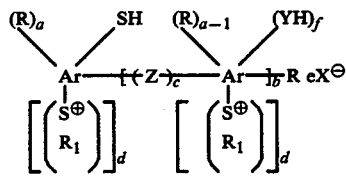

wherein each Ar is independently a cyclic aromatic polyyl, each Y is independently sulfur or oxygen, each R is independently a suitably inert monovalent radical capable of existing as a ring substituent on Ar, each R$_1$ is independently a suitably inert divalent organic radical capable of forming a heterocyclic ring containing —S⊖— in which heterocyclic ring any other heteroatom is S or O, each Z is independently a suitably inert divalent radical bridging the substituted Ar groups, X is a neutralizing anion, each a is independently a positive number corresponding to the number of remaining available ring positions on Ar, b is 0 or a positive number, c is 0 or 1, each d is independently 1 or Z, e is a number such that the salt is electrically neutral and each f is independently 0 or 1.

2. An ar-cyclic sulfonium arylsulfide represented by the formula:

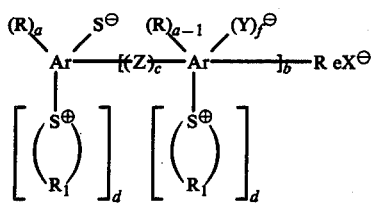

wherein each Ar is independently a cyclic aromatic polyyl, each Y is independently sulfur or oxygen, each R is independently a suitably inert monovalent radical capable of existing as a ring substituent on Ar, each R₁ is independently a suitably inert divalent organic radical capable of forming a heterocyclic ring containing —S⊖— in which heterocyclic ring any additional heteroatom is S or O, each Z is independently a suitably inert divalent radical bridging the substituted Ar groups, X is a neutralizing anion, each a is independently a positive number corresponding to the number of remaining available ring positions on Ar, b is 0 or a positive number, c is 0 or 1, each d is independently 1 or Z, e is a number such that the salt is electrically neutral and each f is independently 0 or 1, said arylsulfide capable of polymerizing upon exposure to thermal or radiation energy which is less than that required to polymerize a similar areneoxide bearing an anionic oxide instead of the anionic sulfide as in said arylsulfide.

3. The arylsulfide of claim 2 wherein each Ar is independently of polyyl of benzene, naphthalene, anthracene or phenanthrene; each R is independently H, Cl, Br, OH, —OR' or —SR' where R' is hydrocarbyl or substituted hydrocarbyl wherein each substituent is independently Cl, Br, OH, —OR' or —SR';

is a 5- or 6-membered heterocyclic ring; each R₁ is independently hydrocarbylene, heterohydrocarbylene wherein the hydrocarbon chain is interrupted by oxygen or sulfur or substituted forms thereof wherein each substituent of R₁ is independently a monovalent radical equivalent to R provided that R₁ has two terminal methylene carbons bonded to the

each Z is independently —O—, —S—,

—R₃—, —OR₃O—, —SR₃S—, —R₃O—, —R₃S—, and

wherein R₃ is hydrocarbylene or substituted hydrocarbylene wherein each substituent of R₃ is independently a monovalent radical equivalent to R, b is 0-5, d is 1, and f is 1.

4. The arylsulfide of claim 3 represented by the formula:

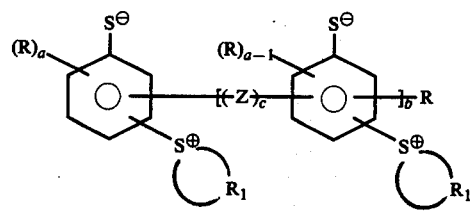

wherein each R is independently H, OH, C₁-C₈ alkyl, or C₁-C₈ alkoxy;

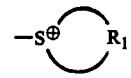

is substituted in a ring position that is ortho or para to —S⊖; each R₁ is independently alkylene, alkyleneoxyalkylene or substituted alkylene wherein each substituent is independently OH, R' or OR' wherein R' is alkyl provided that the terminal carbons of R₁ are methylene; each Z is independently —O—, —S—, —O(C_mH_{2m})O—, —CH₂— or

wherein R'' is C₁-C₄ alkyl and M = 1 to 4; a is 3 or 4; b = 0 to 5; and c = 0 or 1.

5. The arylsulfide of claim 4 wherein each R other than hydrogen is C₁-C₄ alkyl.

6. The arysulfide of claim 4 wherein each R is hydrogen.

7. The arylsulfide of claim 4 represented by one of the following formulas:

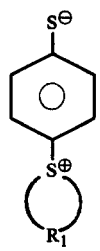 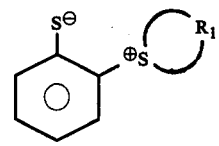

or

-continued

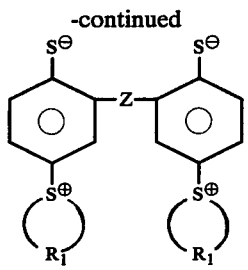

8. The arylsulfide of claim 4 represented by the structural formula:

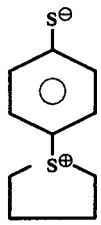

9. The mercaptoarene salt of claim 1 wherein each R is independently H, Cl, Br, OH, —OR' or —SR' where R' is hydrocarbyl or substituted hydrocarbyl wherein each substituent is independently Cl, Br, OH, —OR' or —SR';

$$\underset{\oplus}{\overset{|}{S}}\\ R_1$$

is a 5- or 6-membered heterocyclic ring; each $R_1$ is independently hydrocarbylene, heterohydrocarbylene wherein the hydrocarbon chain is interrupted by oxygen or sulfur or substituted forms thereof wherein each substituent of $R_1$ is independently a monovalent radical equivalent to R provided that $R_1$ has two terminal methylene carbons bonded to the

each Z is independently —O—, —S—,

—$R_3$—, —O$R_3$O, —S$R_3$S—, —$R_3$O—, —$R_3$S—, and $$\overset{O}{\underset{\|}{-CR_3-}}$$

wherein $R_3$ is hydrocarbylene or substituted hydrocarbylene wherein each substituent of $R_3$ is independently a monovalent radical equivalent to R.

10. The arylsulfide of claim 2 wherein each R is independently H, Cl, Br, OH, —OR' or —SR' where R' is hydrocarbyl or substituted hydrocarbyl wherein each substituent is independently Cl, Br, OH, —OR' or —SR';

$$\underset{\oplus}{\overset{|}{S}}\\ R_1$$

is a 5- or 6-membered heterocyclic ring; each $R_1$ is independently hydrocarbylene, heterohydrocarbylene or substituted forms thereof wherein each substituent of $R_1$ is independently a monovalent radical equivalent to R provided that $R_1$ has two terminal methylene carbons bonded to the

each Z is independently —O—, —S—,

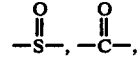

—$R_3$—, —O$R_3$O—, —S$R_3$S—, —$R_3$O—, —$R_3$S—, and $$\overset{O}{\underset{\|}{-CR_3-}}$$

wherein $R_3$ is hydrocarbylene or substituted hydrocarbylene wherein each substituent of $R_3$ is independently a monovalent radical equivalent to R.

11. A polymer obtained by heating the arylsulfide of claim 1.

12. A polymer obtained by heating the arylsulfide of claim 4.

13. The polymer of claim 12 in the form of a solid polymer film.

14. A solid polymer film of the polymer of claim 12 bonded to a metal substrate.

* * * * *

UNITED STATES PATENT AND TRADEMARK OFFICE
CERTIFICATE OF CORRECTION

PATENT NO. : 4,130,543
DATED : December 19, 1978
INVENTOR(S) : George A. Doorakian and Lawrence G. Duquette It is certified that error appears in the above-identified patent and that said Letters Patent are hereby corrected as shown below:

Column 2, line 38, delete "i.e.," and insert --e.g.,--.

Column 3, line 24, delete "Preferably" and insert --wherein--.

Column 3, line 25, delete "Preferablly" and insert --Preferably--.

Column 8, line 1, delete entire formula and rewrite as follows:

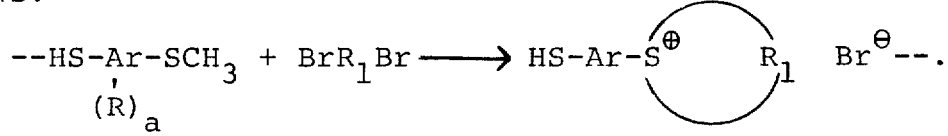

Column 13, line 29, delete "-S$^{\ominus}$-" and insert -- -S$^{\oplus}$- --.

Column 13, line 51, delete entire formula and rewrite as follows:

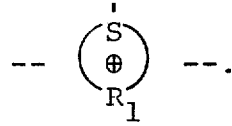

UNITED STATES PATENT AND TRADEMARK OFFICE
CERTIFICATE OF CORRECTION

PATENT NO. : 4,130,543

DATED : December 19, 1978

INVENTOR(S) : George A. Doorakian and Lawrence G. Duquette

It is certified that error appears in the above-identified patent and that said Letters Patent are hereby corrected as shown below:

Column 14, line 53, delete "arysulfide" and insert --arylsulfide--.

Column 15, line 32, delete entire formula and rewrite as follows:

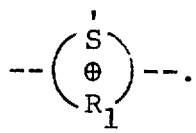

Column 16, line 16, delete entire formula and rewrite as follows:

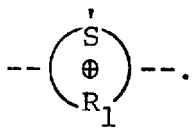

Signed and Sealed this

Thirteenth Day of January 1981

[SEAL]

Attest:

SIDNEY A. DIAMOND

Attesting Officer

Commissioner of Patents and Trademarks